United States Patent
Feitelson et al.

[11] Patent Number: 6,087,556
[45] Date of Patent: Jul. 11, 2000

[54] TRANSGENIC ANIMALS CAPABLE OF REPLICATING HEPATITIS VIRUSES AND MIMICKING CHRONIC HEPATITIS INFECTION IN HUMANS

[75] Inventors: Mark Feitelson, North Wales, Pa.; Linda Siracusa, Cherry Hill, N.J.

[73] Assignee: Thomas Jefferson University, Philadelphia, Pa.

[21] Appl. No.: 09/003,200

[22] Filed: Jan. 7, 1998

Related U.S. Application Data

[63] Continuation-in-part of application No. 08/641,803, May 2, 1996, abandoned.

[51] Int. Cl.[7] .............................. C12N 15/09; C12N 5/10; A61K 49/00
[52] U.S. Cl. .................................... 800/18; 800/3; 800/25
[58] Field of Search ............................... 800/2, 3, 18, 14, 800/25; 435/375, 172.3, 69.1, 320.1; 424/9.1, 9.2, 93.1, 93.21

[56] References Cited

PUBLICATIONS

Houdebine, L. "Production of pharmaceutical proteins from transgenic animals," J. of Biotechnology, vol. 34:269–287, 1994.

Wall, R.J. "Transgenic Livestock: Progress and Prospects for the Future," Theriogenology, vol. 45: 57–68, 1996.

Strojek and Wagner, "The Use of Transgenic Animal Techniques for Livestock Iprovement," Genetic Engineering: Principles and Methods, vol. 10: 221–246, 1988.

Kappel et al. "Regulating Gene Expression in Transgenic Animals," Current Opinion in Biotechnology, vol. 3: 548–553, 1992.

Paul, W.E. Fundamental Immunology. 3rd Edition. Raven Press, New York, New York, 1993.

Kawamura et al. Transgenic expression of hepatitis C virus structureal proteins, Hepatology, 24 (4Part 2), 263A, abstract 547, 47th Annual Meeting and Postgraduate Courses of the American Association for the Study of Liver Diseases, Nov. 8–12, Nov. 1996.

Huang et al. Gene Targeting Technology for Creating Transgenic Models of Lymphopoieses, vol. 43, No. 2: 156–159, Apr. 1993.

*Primary Examiner*—Karen M. Hauda
*Attorney, Agent, or Firm*—Reed Smith Shaw & McClay LLP

[57] ABSTRACT

Transgenically modified animals which replicate hepatitis viruses are provided for use in evaluating virus-chemical and virus-drug interactions in chronic hepatitis infections.

8 Claims, No Drawings

TRANSGENIC ANIMALS CAPABLE OF REPLICATING HEPATITIS VIRUSES AND MIMICKING CHRONIC HEPATITIS INFECTION IN HUMANS

INTRODUCTION

This application is a continuation-in-part of application Ser. No. 08/641,803, filed May 2, 1996, now abandoned.

BACKGROUND OF THE INVENTION

Infection by hepatitis viruses such as hepatitis B virus (HBV) and hepatitis C virus (HCV) is a worldwide health problem.

The World Health Organization (WHO) lists hepatitis B as the ninth leading cause of death worldwide and it has been estimated that 300 million people are chronic carriers of the virus (Hoffnagle *N. Engl. J. Med.* 1990, 323:337–339). Estimates of hepatitis B infection in the United States alone reaches one million. Chronic hepatitis B infection leads to cirrhosis and hepatocellular carcinoma and, if left untreated, death.

The HBV virion comprises an envelope and a nucleocapsid containing a circular, partially double stranded DNA which replicates via an RNA intermediate (Tiollais *Nature* [London] 1985, 317:489–495). The envelope carries the hepatitis B surface antigen, and the nucleocapsid is formed by the hepatitis B core antigen. When virions are present in the blood, an additional antigen, hepatitis B e antigen is detected. Studies have suggested that HBV is not directly cytopathic and that the host immune response to viral antigens presented on the plasma membrane of infected liver cells may play an important role in the pathogenesis of the virus (Mondelli et al. *J. Immunol.* 1982, 129:2773–2778; Chisari et al. *Microb. Pathol.* 1989, 6:311–325). Despite the progress in understanding the course of the infection, the molecular mechanisms responsible for hepatocyte death and viral clearance are not well understood because of the narrow host range of HBV and its nontransmissibility in routine cell culture systems.

The chronic carrier state has been successfully established by experimental infection of chimpanzees with HBV or HBV DNA. However, infection in these animals is self-limiting. In addition, chimpanzees are both expensive and endangered (Barker et al. *J. Infect. Dis.* 1973, 127:648–662; Will et al. *Proc. Acad. Natl. Sci.* 1985, 82:891–895).

HBV-like viruses have also been isolated and characterized in other animals such as ground squirrels, wood chucks, ducks, and tree squirrels (Feitelson et al. *Proc. Natl. Acad. Sci.* 1986, 83:2233–2237; Marion et al. *Proc. Natl. Acad. Sci.* 1980, 77:2941–2945; Mason et al. *J. Virol.* 1980, 36:829–836; Summers et al. *Proc. Natl. Acad. Sci.* 1978, 75:4533–4537). These model systems have provided much information about the biology of the HBV, including information regarding the carrier state. However, the expense and difficulty in handling these animals has limited their use.

More recently, attempts have been made to develop a model system using transgenic mice. However, in all of these transgenic lines, the mice are tolerant to HBV and disease does not develop (Takashima et al. *Immunology* 1990, 75:398–405; Moriyama et al. *Science* 1990, 248:361–364; Farza et al. *J. Virol.* 1988, 62:4144–4152; Araki et al. *Proc. Natl. Acad. Sci.* 1989, 86:207–211). Further, the induction of hepatitis in these mice has required multi-step procedures, such as the priming of lymphocytes with HBV protein in syngeneic mice and the adoptive transfer of these cells in vivo (Moriyama et al. *Science* 1990, 248:361–364). This tolerance to HBV makes it difficult to explore the relationship between immune responses and the overall host-virus relationship in these models. Hence, the host-virus relationship in these mice does not resemble that of human carriers with chronic liver disease. In addition, these transgenic lines are limited as model systems because they replicate virus at low levels (Farza et al. *J. Virol.* 1988, 62:4144–4152; Araki et al. *Proc. Natl. Acad. Sci.* 1989, 86:207–211). Further, the types of viral antigens present and replication of virus in the transgenic animals do not parallel that of a "natural infection". Araki et al. and Farza et al. indicate that this is due to a large region of the HBV DNA in the non-expressing transgenic animals being methylated, i.e., not capable of being expressed. Araki et al. also suggest that integration sites of the introduced DNA on the host chromosome may also have affected expression, resulting in a non-typical HBV infection. Modification of the injected sequence to improve virus expression (to parallel a normal infection) in transgenic animals is suggested.

Transgenic mice that demonstrate a high level of HBV replication comparable to that of infected livers of patients with chronic hepatitis were developed by Guidotti et al. (*J. Virol.* 1995, 69:6158–6169). Guidotti et al. showed expression of a specific transcript which is not indicative of normal HBV infection. These transgenic mice also fail to show progression to a disease state, again limiting their usefulness as a model system.

Another approach to generating a hepatitis animal model has been directly injecting HBV DNA into the liver of animals and monitoring the progression of the infection. For example, rat livers were transfected in vivo with a replication competent HBV construct using a cationic lipid (Takahashi et al. *Proc. Natl. Acad. Sci. USA* 1995, 92:1470–1474). These rats developed histological and serological changes comparable to HBV-induced acute hepatitis in humans. Intrahepatic injection of HBV was also performed in nude mice (Feitelson et al. *J. Virol.* 1988, 62:1408–1415). It was found that HBV infection in nude mice parallels that of HBV-infected chronic carriers (i.e., presence of virus antigens in blood and in the liver). These nude mice also develop lesions in the liver consistent with the presence of chronic hepatitis as seen in long term HBV infected patients. However, this model is not efficient for studying chronic HBV infection and assessing possible therapeutic treatments for chronic HBV infection due to large and uncontrolled variations in individual animals' viral gene expression, viremia, and liver disease.

Hepatitis C virus is also a leading cause of acute and chronic hepatitis, cirrhosis and hepatocellular carcinoma. HCV is a positive-strand RNA virus belonging to the Flaviviridae family, The genome of the virus comprises approximately 9500 nucleotides and contains a single open reading frame that spans the entire genome and encodes a large viral polypeptide of 3010 amino acids (Houghton et al. *Hepatology* 1991, 14:381–388). Upon infection of mammalian cells, RNA of the virus is translated into a single continuous polyprotein that is proteolytically processed by host signal peptidase and two viral proteases to produce at least 10 structural and non-structural proteins (Shimotohno et al. *J. Hepatol.* 1995, 22:87–92). The genome also contains a highly conserved 5' untranslated region that functions as an internal ribosome entry site for translation of the viral genome (Wang, C. and Siddiqui, A. *Curr. Top. Microbiol. Immunol.* 1995, 203:99–105). The HCV genome also contains a short 3' untranslated and a homopolymer tail of A or U residues after the open reading frame (Takamizawa et al.

J. Virol. 1991, 65:1105–1113). A highly conserved 98 nucleotide non-homopolymeric sequence at the 3' end of the HCV RNA genome has also been identified (Kolykhalov et al. J. Virol. 1996, 70:3363–3371; Tanaka et al. J. Virol. 1996, 70:3307–3312).

An in vitro system for HCV propagation has been developed to characterize virus replication, virus persistence and viral pathogenicity. In this system, HCV replication was established in vitro by gene transfer of infectious HCV cDNA into HepG2 cells (Hiramatsu et al. J. Viral Hepatitis 1997, 4(Suppl. 1):61–67; Dash et al. American J. Pathology, 1997 151:363–373).

Further, several features of the human HCV infection have been found to be recapitulated in a chimpanzee model (Walker, C. M. Springer Semin. Immunopathol (Germany) 1997, 19(1):85–98). Frequency of persistent infection is high in both humans and chimpanzees. Viral replication also occurs despite evidence of cellular and humoral responses. However, the necroinflammatory lesions that develop in chronically infected chimpanzees are almost always mild, whereas in humans these lesions can range from mild to severe liver inflammation and endstage cirrhosis requiring transplantation. Further, the availability of this primate for research is strictly limited.

Accordingly, a number of transgenic mouse models for the study of HCV have been developed. For example, two independent transgenic mouse lines carrying the HCV core gene have been established to clarify whether or not the HCV core protein has an effect on pathological phenotypes in the liver (Moriya et al. J. Gen. Virol. 1997, 78(7):1527–31). These mice developed progressive hepatic steatosis, indicating that the HCV core protein plays a direct role in the development of hepatic steatosis, which characterizes hepatitis C.

Transgenic mice carrying the HCV gene envelope genes have also been shown to express the HCV envelope proteins in organs, including the liver and salivary glands (Koike et al. Proc. Natl Acad. Sci. USA 1997, 94(1):233–6). Further analysis of these animals has revealed that they develop exocrinopathy involving the salivary and lachrymal glands which resembles the pathology of Sjogren syndrome. Sjogren syndrome has been suggested to have a possible association with chronic hepatitis C. Accordingly, this transgenic mouse system is suggested to be a good animal model for the study of HCV infection.

However, there is a need for animal models that parallel the course of hepatitis virus infections in humans and approximate the evolution of a chronic carrier state which can be used in assessing possible therapeutic treatments for chronic infection by these viruses in humans.

SUMMARY OF THE INVENTION

An object of the present invention is to provide an animal model for studying chronic hepatitis virus infection in animals that are not tolerant to hepatitis viral antigens which comprises an immunodeficient mouse transgenically modified to contain an integrated hepatitis virus DNA so that a hepatitis virus gene is expressed and the hepatitis virus is replicated in the mouse. In a preferred embodiment, the transgene is for the entire hepatitis B virus or hepatitis C virus genome and is introduced into SCID mice. A selected immune system component can then be introduced into the animals of the present invention by adoptive or passive transfer of primed donor splenocytes so that the animals can be used in methods of evaluating virus-chemical, virus-drug and virus-immunomodulating agent on the hepatitis virus-host relationship.

DETAILED DESCRIPTION OF THE INVENTION

A transgenic animal model for hepatitis viral infections has now been developed in severe combined immunodeficient (SCID) mice. The generation of these transgenic animals containing integrated hepatitis virus DNA allows for the assessment of anti-viral and immunomodulatory intervention therapies, including the screening of drug candidates. These animals can also be used to analyze the virus-host relationship, evaluate the relationship between the virus and chemicals metabolized and/or detoxified by the liver, and identify cellular biochemical pathways contributing to the development and progression of chronic liver disease.

In a preferred embodiment, the transgene introduced into these animals is the entire hepatitis B virus or hepatitis C virus genome. For example, CB.17 SCID mice are made transgenic by microinjection of full length replication competent HBV DNA. In a further embodiment, a selected immune system component is introduced into these animals by adoptive or passive transfer of primed donor splenocytes. In similar fashion, a full length replication competent HCV DNA such as that described by Hiramatsu et al. J. Viral Hepatitis 1997, 4(Suppl. 1):61–67 or Dash et al. American J. Pathology, 1997 151:363–373) can be microinjected into immunodeficient mice to produce a model for chronic HCV infection.

For the construction of transgenic mice and other animals, the DNA to be microinjected is purified by agarose gel electrophoresis. The band of interest is then electrophoretically transferred to a DEAE membrane, eluted, extracted with phenol/chloroform, then with chloroform and precipitated with ethanol. The extractions are repeated, the DNA quantitated and stocks prepared for microinjection.

In a preferred embodiment, the isolated, purified DNA is microinjected into the mouse ova by standard techniques. Pseudopregnant CB.17 SCID females are implanted with approximately 16 microinjected ova by techniques known to those of skill in the art. The pups that are born are analyzed for transgene integration into cellular DNA by Southern blot hybridization. Blood from the positive founder is then assayed for virus. To assay virus, mouse serum is layered on a 5%–20% sucrose gradient, and centrifugation is carried out to equilibrium. Fractions are assayed for virus by immunoprecipitation with anti-HBs and polymerase chain reaction of the pellet. Polymerase chain reaction (PCR) generated signals are obtained only at gradient fractions characteristic of the virus, suggesting that circulating virus is present in the blood.

The founder transgenic mice ($F_0$) are then mated with additional SCID mice (C3H/SCID strain). Progeny ($F_1$) from this mating are tested for the transgene and presence of the virus in blood via PCR as previously described. Positive results indicate that the functional transgene has been transmitted from one generation to another ($F_0$ to $F_1$). The positive $F_1$ mice are then mated with each other to increase the number of transgenic C3H/SCID mice. The presence of circulating virus is verified as described above.

The transgenic mouse model of the present invention provides an opportunity to understand the development of antiviral immunity from a nontolerant context for the first time. In contrast, immunocompetent HBV transgenic mice described in the art have all been tolerant to HBV antigens. Accordingly, these mice do not develop the disease, making is virtually impossible to study the immune-mediated pathogenesis of chronic infection in these mice. Tolerance to these antigens does not develop in humans acutely infected with the virus. Nor does it develop in the mice of the present invention. Accordingly, the mice of the present invention represent a qualitatively different approach to the analysis of the host-virus relationship which develops as the immune system recognizes and responds to virus infected cells after adoptive or passive transfer.

The animals of the present invention can be further modified to be capable of exhibiting different, specific immune responses. In one embodiment, a selected immune system component is introduced into these animals by adoptive transfer or passive transfer of primed donor splenocytes in accordance with well known techniques. Alternatively, transgenic mice of the present invention can be bred with other strains of mice having selected immune deficiencies or lacking in one or more host genes suspected to be important to virus pathogenesis, mice having selected components of the immune response tolerant to the virus can be obtained. For example, breeding of C3H/SCID transgenic mice with the same strain of nude mice will allow for the assessment of the role or roles that B cell tolerance plays in viral expression/replication and pathogenesis. Alternatively, the human tumor suppressor gene, p53, is important in sustaining high levels of HBV replication and its inactivation is associated with malignant transformation. Thus, in another example, mice of the present invention which replicate HBV, can be mated with p53 "knockout" mice to evaluate the host-virus relationship in their progeny. Mating to other selected "knockout" mice may help to define the role of other cellular genes in the pathogenesis of chronic infection and hepatocellular carcinoma. Alternatively, if the appropriate mice for mating are not available, the transgenic mice of the present invention can be further transgenically modified to produce mice capable of expressing specific genes or could be used as starting points for selected gene knockout experiments.

Interactions of the virus with chemicals, drugs and/or immune modulating agent interactions can then be evaluated in this animal model by administering a chemical or drug to be evaluated to the animal of the present invention having no anti-viral immune responses and again to animals of the present invention to which anti-viral immune response have been restored. These animals can be used to evaluate viral interactions with other hepatotoxic (but non-carcinogenic) chemicals such as ethanol in the presence and absence of an immune response. Animals can be evaluated for the development and progression of liver disease. Liver disease is monitored histologically and by elevated levels of alanine aminotransferase (ALT) and or gamma glutamyltransferase in serum. Further, the patterns of viral gene expression and replication in the presence of such chemicals can be analyzed. These animals can also be used to evaluate the patterns of viral replication and gene expression in the presence of putative anti-viral drugs and in the presence of antisense or ribozyme gene therapy approaches against the virus. In all of these cases, virus gene expression is tested by immunohistochemistry, Southern and Northern blotting, as well as in situ hybridization in the liver. Serum is tested for virus by polymerase chain reaction and enzyme linked immunosorbent assay. In addition, gene therapy or anti-viral nucleic acid constructs can be delivered to the liver through liver specific molecules such as the asialoglycoprotein receptor in the absence of immune responses against either the virus (HBV or HCV) or the vector (e.g., polylysine carrier, recombinant adenovirus or SV40). Potential therapeutic approaches against selected host biochemical pathways modified by the virus can also be evaluated.

In addition, the effects of hepatitis virus on hepatic metabolism can be elucidated. In this method, a chemical or drug known to be metabolized primarily by the liver is administered to a transgenic animal. One example of a chemical or drug primarily metabolized by the liver is ethanol. The effects of the hepatitis virus upon ethanol mediated lipid peroxidation, alcohol dehydrogenase activity, NFKB activation, and acetaldehyde and free radical formation can be directly measured in the liver of such animals in accordance with well known procedures. In addition, the effect of virus upon the metabolism of aflatoxin, a known hepatocarcinogen, can be monitored by testing for the presence of aflatoxin DNA adducts in the liver and aflatoxin albumin adducts in the blood and urine. Many other compounds well known to those of skill in the art can also be evaluated in this context. These results are then compared to the metabolism of the same drug or chemical in a control animal. By "control animal" it is meant an animal of the same species as the transgenic animal but which has not been transgenically modified.

These transgenic animals can also be used to assess patterns of liver disease in the presence of immune system modulating drugs which do not specifically have anti-viral activities. Examples of immune system modulating drugs include, but are not limited to, interferon, tumor necrosis factor, transforming growth factor and interleukins. The sensitivity of virus-infected hepatocytes to the action of environmental carcinogens (chemical or viral) can also be evaluated as illustrated with aflatoxin in the preceding paragraph. Virus-virus interactions and their effect on the pathogenesis of liver disease can also be studied by mating transgenic mice of the present invention expressing and replicating hepatitis virus with transgenic mice expressing other viruses. Elucidation of the biochemical pathways altered in the hepatocyte by the virus can also be performed in this animal model by creating a difference library or differential display which reveals clones whose expression is altered in the presence of virus. Further, the immune system components which are responsible for liver disease, such as T cells, B cells or subsets of these cell types, and the immune responses necessary for termination of the chronic carrier state by adoptive transfer of appropriately primed donor splenocytes can be determined.

Viral replication and gene expression is, in part, hormone dependent (Farza et al. *Proc. Natl. Acad. Sci.* 1987, 84:1187–1191). The influence of hormones upon the host-virus relationship can be evaluated in the animal model of the present invention in the absence or presence of intact anti-viral immune responses. For example, the patterns of viral expression and levels of replication can be evaluated in liver and serum after hormone treatment and compared to that of untreated animals.

While the examples provided in this specification primarily describe HBV and HCV transgenic mice, it will be obvious to those of skill in the art upon reading this disclosure that the protocol for generating these animals can be applied to study the role of the immune response(s) against a variety of transgenes for which these mice are not tolerant. Accordingly, the animal model of the present invention can be utilized in a wide variety of immunologically mediated diseases. Further, it is believed that the present invention is also applicable to SCID or other immunodeficient animals. By "animal" it is meant to include, but is not limited to, mammals, fish, amphibians, reptiles, birds, and marsupials. Rodents such as rats, guinea pigs, hamsters and mice are preferred.

The following nonlimiting examples are provided to further illustrate the present invention. These examples are specifically related to production of transgenically modified mice which replicate hepatitis B virus. However, the methods described herein are also applicable to production of transgenically modified mice which replicate hepatitis C virus.

EXAMPLES

Example 1

Isolation and Purification of DNA Suitable for Microinjection into Mouse Zygotes Full length HBV DNA from the clone X"A", which is a head-to-tail dimer of HBV cloned into pBR322 and is known to replicate virus in transiently transfected HepG2 cells, was used. HepG2 is a differentiated tumor cell line isolated from the liver of a patient with hepatoblastoma, which is known to be permissive for HBV replication. A restriction digest was performed to liberate the DNA insert from the vector sequences. The DNA digest was then electrophoresed in a TAE gel. Two pieces of NA-45 paper (DEAE membrane, S&S) were cut and inserted into the gel just behind and just in front of the desired band. When the desired band is larger than the vector band, the polarity of the leads is reversed and the gel is run backwards at 100 mA so that the band runs into the NA-45 paper. The upper piece of paper contains the insert. When the desired band is smaller than the vector band, the gel is run forward so that the band runs into the lower piece of paper.

The paper was removed and placed in a microfuge tube containing a sufficient amount of 1 M NaCl/0.05 M arginine free base to keep the paper covered. The tube was incubated at 65° C. to 70° C. for approximately 2 hours to elute the DNA. The eluent was removed and extracted with phenol/chloroform followed by chloroform alone. The eluent was then precipitated twice with ethanol and NaAcetate. The DNA pellet was resuspended in injection buffer (10 mM Tris, pH 7.5, 0.1 mM EDTA) and the extraction and precipitation steps were repeated. The final pellet was washed with 70% ethanol and dried. The DNA was resuspended in injection buffer and quantitated.

Example 2

Microinjection of DNA and Establishment of Transgenic Mouse Strains

Embryo donors were female CB.17 SCID mice superovulated with 5 IU of pregnant mare serum (PMS) and human chorionic gonadotropin (HCG) in sterile saline mated to stud male mice. Embryos were obtained on day 0.5 of pregnancy, i.e., the day a copulatory plug is found. Females that had successfully mated as evidenced by the presence of a copulatory plug were euthanized and the fallopian tubes bearing the embryos sterilely removed. The embryos were flushed from the oviducts using a 30 gauge needle into Whittens 640 media containing hyaluronidase to remove the adhering follicle cells and supernumery sperm from the embryos. The embryos were kept at 37° C. on a warming tray. The embryos were washed twice in Whittens media and evaluated for normalcy of development under the dissecting microscope. Normal embryos were placed in culture and held for microinjection the same day.

Approximately 75 embryos were removed at one time from the culture dish and placed in a microdrop of media under paraffin oil in a glass injection chamber. They were placed on an inverted microscope equipped with micromanipulators. The zygotes were manipulated and held in place using a suction pipet attached to one manipulator at 400× magnification. The embryos were oriented with the male pronucleus towards the injection pipet, which is controlled by the second manipulator; the injection pipet was inserted through the zygote membrane into the male pronucleus and one to two picoliters of a sterile pure DNA solution was injected. Once all the zygotes had been injected they were removed from the microinjection apparatus, washed once in Whittens media, and cultured at 37° C. in Whittens media in a 5% $O_2$, 5% $CO_2$, 90% $N_2$ atmosphere overnight.

Recipients were 6 week to 3 month old females that were copulated with vasectomized (sterile) males. These females are pseudopregnant and will bear live pups derived from embryos transferred to their fallopian tubes or uteri. The pseudopregnant recipients were given an intraperitoneal injection of avertin (2% w/v in sterile filtered saline) administered at a dose of 0.15 ml/10 grams body weight. Once the females were anesthetized, part of their backs were shaven, disinfected with 70% alcohol. An incision was made in the skin and the uteri, fallopian tubes and ovary from one or both sides was exposed. The embryos were transferred in sterile Whittens media (containing penicillin and streptomycin) using a sterile transfer pipet into the ampulla, after which these organs were transferred to the body cavity. The incision was then closed with a wound clip and the mice allowed to recover on a 37° C. warming tray. Once recovered, the females were housed singly or in pairs until the litter was born.

Example 3

Analysis of Transgenic Mice for Presence of Transgene and Virus

For transgene detection, whole cell DNA isolated from the pups at 3–4 weeks of age was analyzed by polymerase chain reaction (PCR) followed by agarose gel electrophoresis.

Chromosomal DNA was extracted from mouse tails using a QIA amp tissue kit (QIAGEN, Hilden, Germany). Tissue (0.4 to 0.6 cm pieces of tail) was digested in 180 μl of buffer ATL and 20 μl of proteinase K (17.8 mg/ml) at 55° C. overnight. The supernatant was precipitated by adding 410 μl of buffer AL/ethanol mixture and applied onto the QIA amp column. The column was centrifuged at 6000 g for 1 minute and then washed twice with buffer AW. The DNA was eluted with 200 μl of distilled water.

Forty microliters of the extracted mouse chromosomal DNA were used as a template in a 50 μl reaction mixture containing 10 mM Tris-HCl (pH 8.3), 50 mM KCl, 1.5 mM $MgCl_2$, 0.01% (wt/vol) gelatin, 0.2 mM of each deoxynucleotide (Pharmacia Ltd., Milton Keynes, United Kingdom) and 0.2 μM each of oligonucleotide primer MF03 (5'-ATGGACATCGACCCTTATAAAGAATTTG-3' (SEQ ID NO: 1)) and MF04 (5'-CTAAGATTGAGATCTTCTGCGACGCGG-3' (SEQ ID NO: 2)) and 2.5 units Taq DNA polymerase (Perkin Elmer, Norwalk, Conn.). PCR was performed on a Perkin Elmer thermal cycler 480. The amplification cycle consisted of an initial denaturation of target DNA at 99° C. for 5 minutes followed by denaturation at 94° C. for 1 minute, primer annealing at 55° C. for 1 minute, and extension at 72° C. for 1 minute. Samples were amplified through 35 consecutive cycles. Negative reagent control reactions containing distilled water instead of DNA were performed with each batch of amplification. The amplified products obtained by PCR were analyzed by agarose gel (1.4% wt/vol) electrophoresis.

Bands signifying the presence of the transgene were identified by ethidium bromide staining.

For virus detection, blood samples (50–100 μl) from positive mice were retroorbitally obtained. Serum from the samples was collected following two centrifugations at 14,000 RPM for 15 minutes.

Continuous $CaCl_2$ gradients were prepared. Solutions having densities of 1.19 and 1.40 were prepared. Using a gradient maker, 2.25 ml of each solution were placed in the columns and 4.5 ml of continuous gradient were then poured into Beckman Ultra Clear 13×51 mm tubes. Mouse serum (25 μl) was then carefully layered on top of the gradient. The samples were then spun in an SW55STL rotor in a Beckman L-80 ultracentrifuge at 45,000 RPM for approximately 66.5 hours. The gradient was then fractionated by inserting tygon tubing to the bottom of the tube and withdrawing approximately 15 drops at a time or 0.3 ml into 13 to 15 fractions. Refractive indices of each fraction were measured and fractions of density 1.22 to 1.33 were assayed for virus.

PCR was carried out as outlined above, except that after the first 35 cycles, 10% of each sample was reamplified another 35 cycles. The products from each fraction were then analyzed by agarose gel electrophoresis, as described above, and ethidium bromide staining.

PCR generated signals were obtained only at gradient fractions characteristic of the virus, suggesting that circulating virus is present in the blood. These signals also appeared after PCR amplification of gradient fractions immunoprecipitated with anti-HBs, suggesting that the DNA detected by PCR were encapsidated in enveloped virus particles.

What is claimed:

1. A transgenic immunodeficient mouse that is not tolerant to hepatitis viral antigens wherein the transgenic immunodeficient mouse lacks functional T-cells and B-cells, and wherein the somatic and germ cells of the transgenic immunodeficient mouse contain an integrated hepatitis virus DNA so that hepatitis virus genes are expressed and the hepatitis virus is replicated in the transgenic mouse.

2. The transgenic mouse of claim 1 wherein said immunodeficient mouse is a SCID mouse.

3. The transgenic mouse of claim 1 where the hepatitis virus is hepatitis B virus.

4. The transgenic mouse of claim 1 wherein the hepatitis virus is hepatitis C virus.

5. The transgenic mouse of claim 1 wherein the transgenic mouse comprises a selected immune system component that is introduced into the transgenic mouse by adoptive transfer of primed donor splenocytes or by passive transfer of viral antibodies to cause chronic hepatitis.

6. A method of evaluating interactions of a chemical, drug or immunomodulating agent with a hepatitis virus comprising:
   (a) administering a chemical, drug, or immunomodulating agent to be evaluated to the transgenic mouse of claim 5;
   (b) monitoring levels of viral gene expression and replication and progression of liver disease in the mouse administered the chemical, drug or immunomodulating agent;
   (c) monitoring levels of viral gene expression and replication and progression of liver disease in the transgenic mouse of claim 5 which has not been administered the chemical, drug or immunomodulating agent; and

SEQUENCE LISTING (1) GENERAL INFORMATION:

(iii) NUMBER OF SEQUENCES: 2

(2) INFORMATION FOR SEQ ID NO: 1:

(i) SEQUENCE CHARACTERISTICS:
      (A) LENGTH: 28
      (B) TYPE: Nucleic Acid
      (C) STRANDEDNESS: Single
      (D) TOPOLOGY: Linear (iv) ANTI-SENSE: No (xi) SEQUENCE DESCRIPTION: SEQ ID NO: 1:

ATGGACATCG ACCCTTATAA AGAATTTG       28

(2) INFORMATION FOR SEQ ID NO: 2:

(i) SEQUENCE CHARACTERISTICS:
      (A) LENGTH: 27
      (B) TYPE: Nucleic Acid
      (C) STRANDEDNESS: Single
      (D) TOPOLOGY: Linear (iv) ANTI-SENSE: No (xi) SEQUENCE DESCRIPTION: SEQ ID NO: 2:

CTAAGATTGA GATCTTCTGC GACGCGG       27

(d) comparing the monitored levels of viral gene expression and replication and progression of liver disease in the mouse of step b) with the mouse of step c) so that differences in the level of viral gene expression and replication and progression of liver disease resulting from the chemical, drug or immunomodulating agent can be evaluated.

7. The transgenic mouse of claim 5 wherein the selected immune system component comprises B cells, T cells, subsets of T cells or antibodies against at least one antigen of a hepatitis virus.

8. A method of evaluating interactions of a chemical, drug or immunomodulating agent with a hepatitis virus comprising:

(a) administering a chemical, drug, or immunomodulating agent to be evaluated to the transgenic mouse of claim 1;

(b) monitoring levels of viral gene expression and replication in the mouse administered the chemical, drug or immunomodulating agent;

(c) monitoring levels of viral gene expression and replication in the transgenic mouse of claim 1 which has not been administered the chemical, drug or immunomodulating agent; and (d) comparing the monitored levels of viral gene expression and replication in the mouse of step (b) with the mouse of step (c) so that differences in the level of viral gene expression and replication resulting from the chemical, drug or immunomodulating agent can be evaluated.

* * * * *